(12) United States Patent
Ping

(10) Patent No.: US 7,902,256 B2
(45) Date of Patent: *Mar. 8, 2011

(54) PEST TREATMENT COMPOSITION

(75) Inventor: Jeffrey H. Ping, Cumming, GA (US)

(73) Assignee: Effcon Laboratories, Inc., Marietta, GA (US)

(*) Notice: Subject to any disclaimer, the term of this patent is extended or adjusted under 35 U.S.C. 154(b) by 424 days.

This patent is subject to a terminal disclaimer.

(21) Appl. No.: 11/775,641

(22) Filed: Jul. 10, 2007

(65) Prior Publication Data
US 2008/0015262 A1      Jan. 17, 2008

Related U.S. Application Data

(63) Continuation of application No. 10/276,657, filed as application No. PCT/US01/16367 on May 21, 2001, now Pat. No. 7,282,211.

(60) Provisional application No. 60/205,843, filed on May 19, 2000.

(51) Int. Cl.
*A01N 37/06* (2006.01)

(52) U.S. Cl. ............ 514/549; 424/70.1; 424/70.31; 424/78.02; 424/78.03; 424/78.08; 424/405; 424/406; 514/937

(58) Field of Classification Search ............ 514/549
See application file for complete search history.

(56) References Cited

U.S. PATENT DOCUMENTS

| | | | |
|---|---|---|---|
| 4,193,986 A | 3/1980 | Cox | |
| 4,256,600 A | 3/1981 | Lewis et al. | |
| 4,518,593 A | 5/1985 | Juvin et al. | |
| 4,774,081 A | 9/1988 | Flashinski et al. | |
| 4,774,082 A | 9/1988 | Flashinski et al. | |
| 4,906,488 A | 3/1990 | Pera | |
| 4,927,813 A | 5/1990 | Bernstein | |
| 4,999,187 A | 3/1991 | Vernon | |
| 5,064,859 A | 11/1991 | Crammer et al. | |
| 5,079,000 A | 1/1992 | Takahashi et al. | |
| 5,106,622 A | 4/1992 | Sherwood et al. | |
| 5,227,163 A | 7/1993 | Eini et al. | |
| 5,227,406 A | 7/1993 | Beldock et al. | |

(Continued)

FOREIGN PATENT DOCUMENTS

AU      7137063      12/1971

(Continued)

OTHER PUBLICATIONS

Carson et al., American Journal of Diseases of Children, 1988 (vol. 142) pp. 768-769 "Pyrethrins Combined With Piperonyl Butoxide Rid vs 1 Percent Permethrin Nix in the Treatment of Head Lice" (abstract only).

(Continued)

*Primary Examiner* — Neil Levy
(74) *Attorney, Agent, or Firm* — Sutherland Asbill & Brennan LLP

(57) ABSTRACT

The present invention provides a pediculicidal and ovicidal composition with an extraordinarily lethal effectiveness that can also be used to remove parasites, such as lice. The pediculicidal and ovicidal composition contains a purified terpene agent such as citronellal, citronellol, citronellyl or a mixture thereof, a short chain alcohol, and a non-aqueous co-solvent and/or surfactant component. The composition more preferably utilizes citronellyl acetate as the active agent. The compositions can be administered topically to humans, animals or any infested areas.

18 Claims, 9 Drawing Sheets

U.S. PATENT DOCUMENTS

| | | | |
|---|---|---|---|
| 5,292,528 | A | 3/1994 | Mori et al. |
| 5,298,250 | A | 3/1994 | Lett et al. |
| 5,346,922 | A | 9/1994 | Beldock et al. |
| 5,411,992 | A | 5/1995 | Eini et al. |
| 5,518,736 | A | 5/1996 | Magdassi et al. |
| 5,565,208 | A | 10/1996 | Vlasblom |
| 5,621,013 | A | 4/1997 | Beldock et al. |
| 5,648,398 | A | 7/1997 | Beldock et al. |
| 5,658,584 | A | 8/1997 | Yamaguchi |
| 5,776,477 | A | 7/1998 | Ryder |
| 5,783,202 | A | 7/1998 | Tomlinson et al. |
| 5,792,465 | A | 8/1998 | Hagarty |
| 5,902,595 | A | 5/1999 | Burklow et al. |
| 5,977,186 | A | 11/1999 | Franklin |
| 6,103,248 | A | 8/2000 | Burkhart et al. |
| 6,130,253 | A | 10/2000 | Franklin et al. |
| 6,139,859 | A * | 10/2000 | Precopio ............... 424/406 |
| 6,696,067 | B2 * | 2/2004 | Brandt et al. ............... 424/401 |
| 7,282,211 | B2 * | 10/2007 | Ping ............... 424/406 |

FOREIGN PATENT DOCUMENTS

| | | |
|---|---|---|
| DE | 3901341 | 7/1990 |
| EP | 0 736 251 A1 | 10/1996 |
| FR | 2 759 546 A | 8/1998 |
| FR | 2759546 | 8/1998 |
| JP | 02 142703 A | 5/1990 |
| JP | 05 039203 A | 2/1993 |
| JP | 2000128720 | 10/1998 |
| WO | WO 98/04128 | 2/1998 |
| WO | WO 99/18800 | 4/1999 |
| WO | WO 00/00213 | 1/2000 |
| WO | WO 0005964 | 2/2000 |

OTHER PUBLICATIONS

Mumcuoglu, American Entomologist, 1996 (vol. 42) pp. 175-178 "Control of Human Lice (Anoplura: Pediculidae) Infestations: Past and Present" (abstract only).

E, Haubruge et al., Meded. Fac. Landbouwwet, Rijksuniv Gent (vol. 54 No. 3b) (1989) pp. 1083-1093 "The Toxicity of Five Essential Oils Extracted From Citrus Species with Regard to Stiophilus Zeamais Motsch (Col., Curculionidae), Prostephanus Truncatus (Horn) (Col., Bostrychidae) and Tribolium Castaneium Herbst (Col., Tenebrionidae)" (abstract only).

* cited by examiner

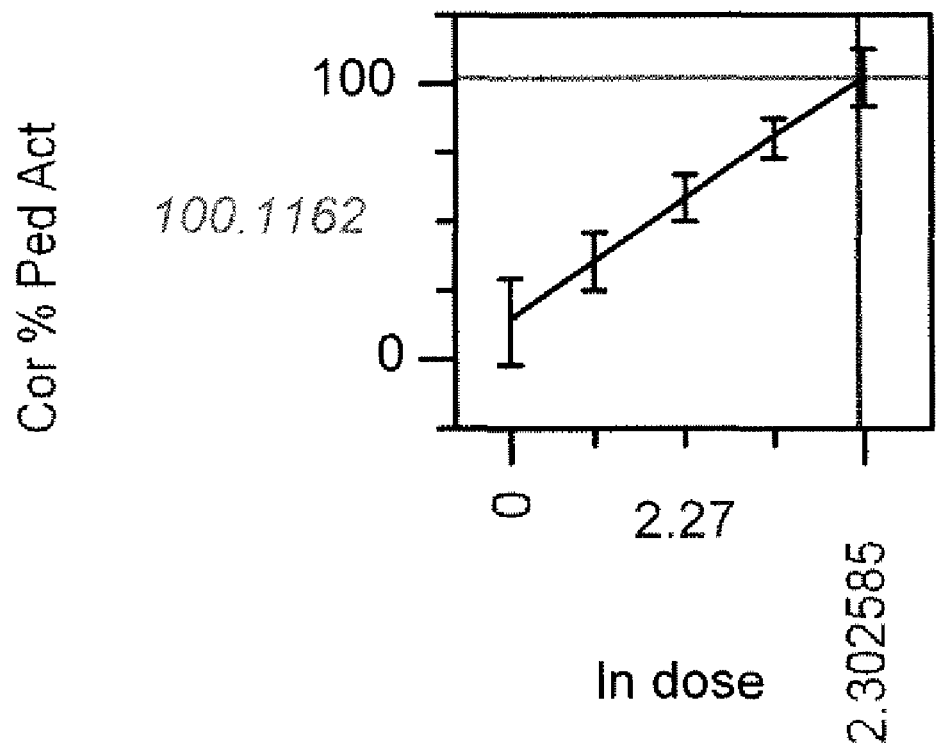
FIG. 4.a.
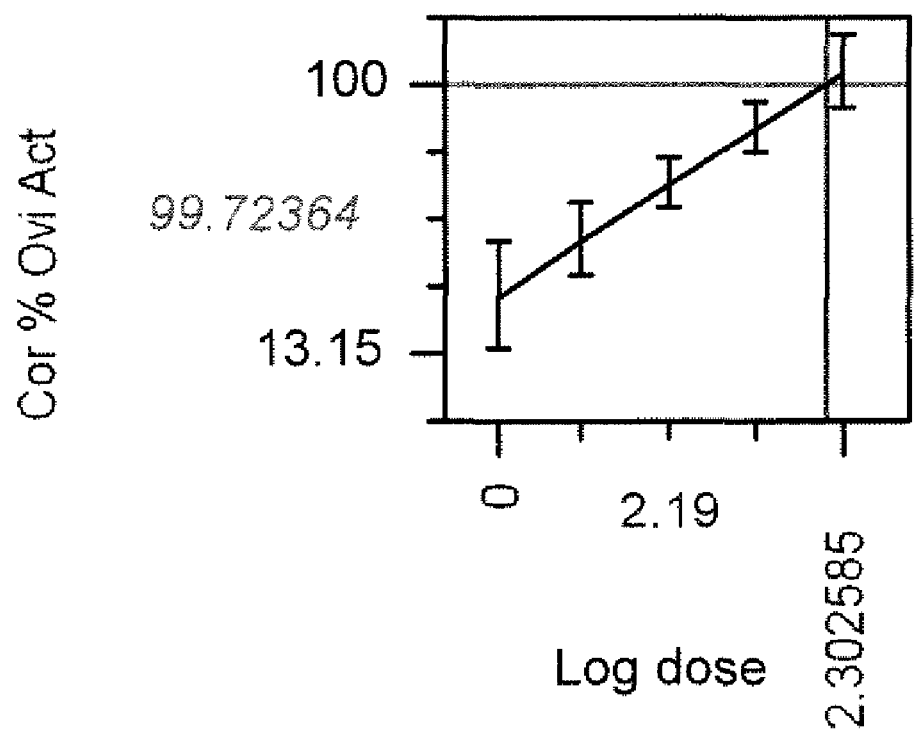
FIG. 4.b.

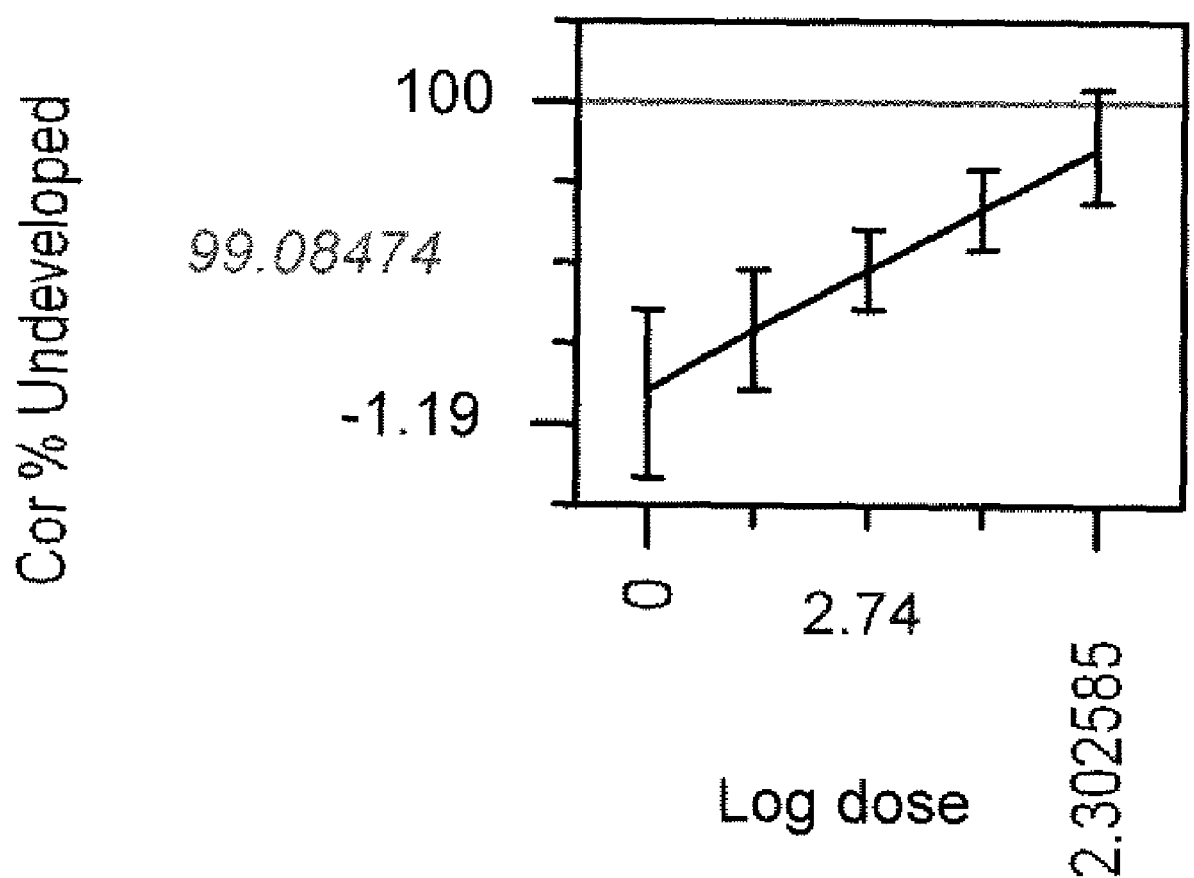
FIG. 4.c.

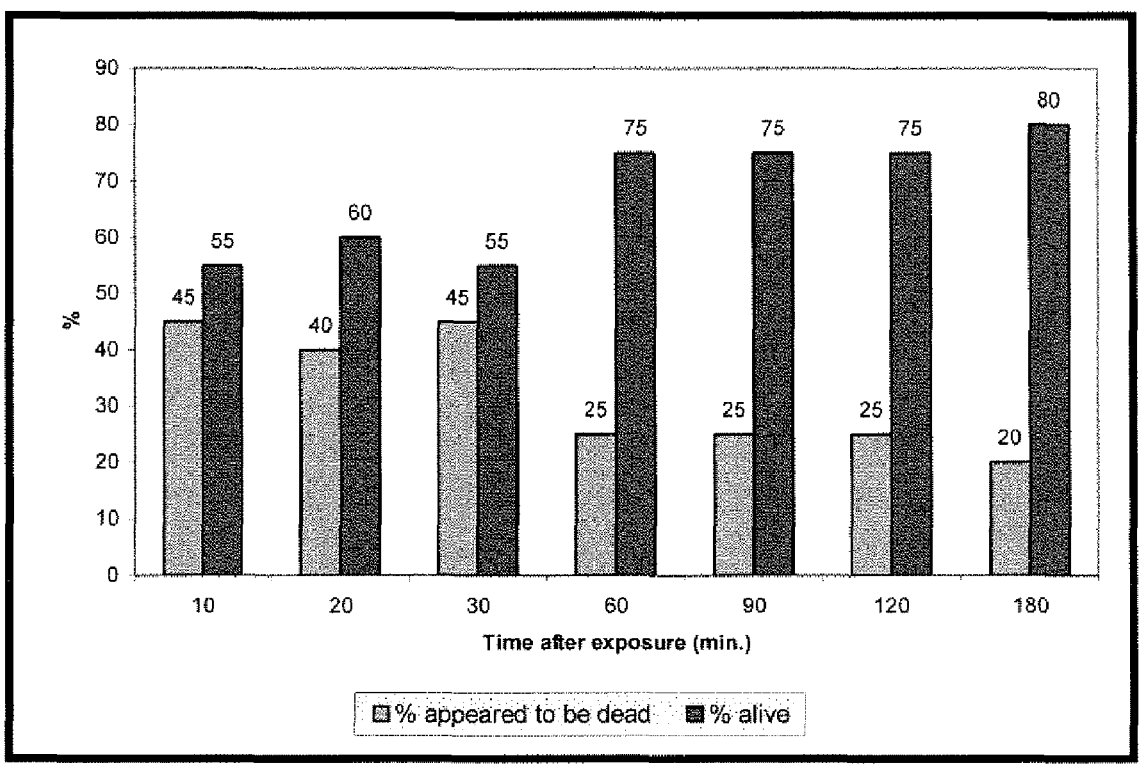
FIG. 7.a.
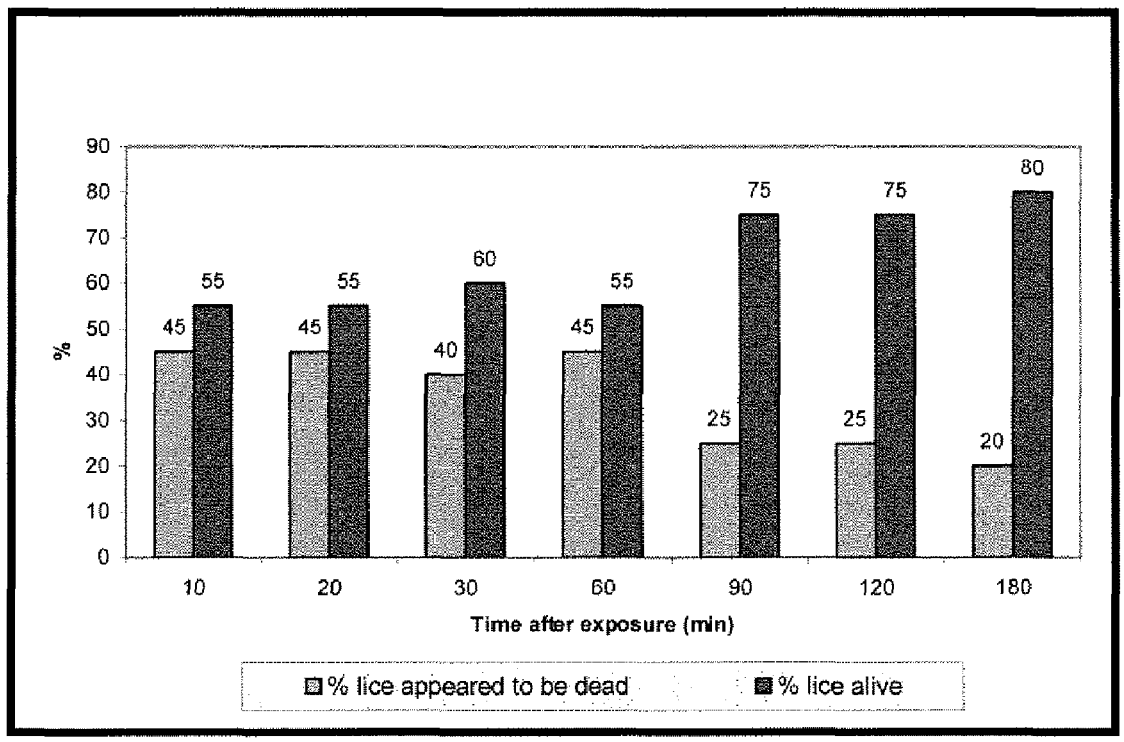
FIG. 7.b.

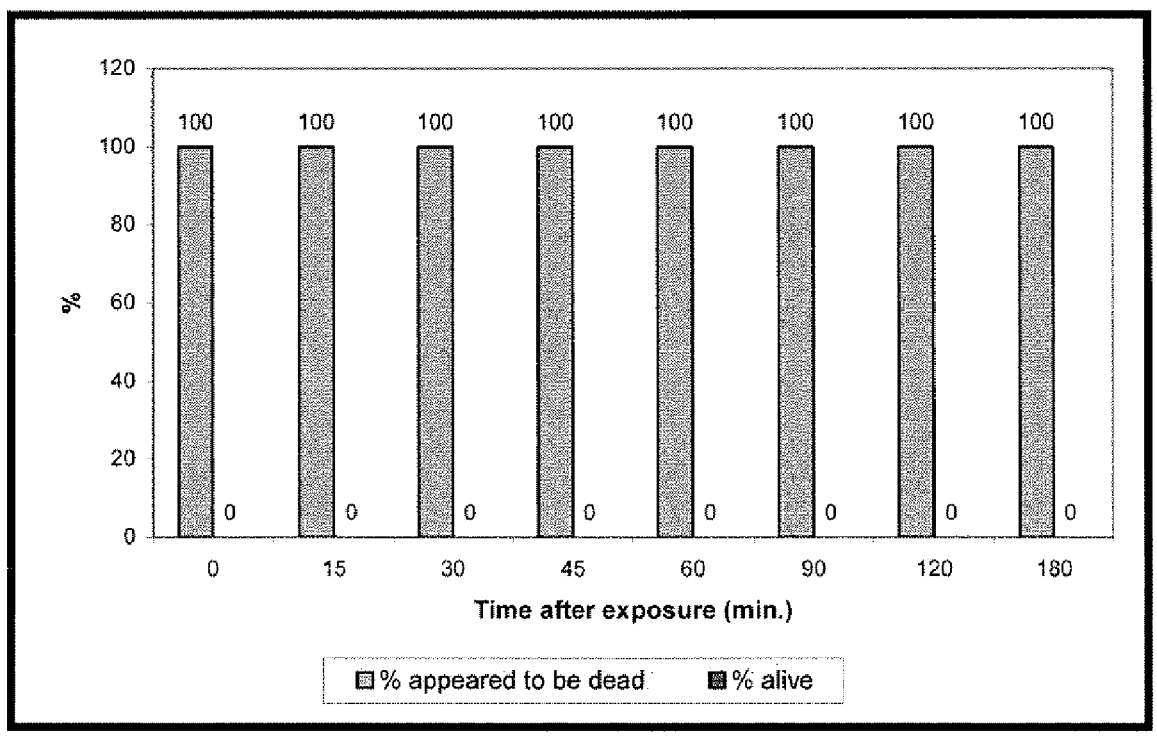
FIG. 7.c.

PEST TREATMENT COMPOSITION

CROSS REFERENCES TO RELATED APPLICATIONS

This application is a continuation of U.S. application Ser. No. 10/276,647 filed on Nov. 18, 2002, now U.S. Pat. No. 7,282,211, which claims priority to PCT Patent Application No. PCT/US01/16367 filed May 21, 2001 and U.S. Provisional Application Ser. No. 60/205,843 filed May 19, 2000.

FIELD OF THE INVENTION

The present invention relates to agents and methods for the treatment of pest infestations. In particular, the invention relates to compositions for cleansing individuals infested with parasites, such as lice, and their ova.

BACKGROUND

Pesticides and insects repellents have long been sought for use against harmful or annoying parasites. Pests such as lice and fleas are irritating and painful to their human and animal hosts, and can also be vectors for other agents of disease. The pesticides and repellents available in the prior art, however, suffer from various deficiencies. Often, compositions provided as insect repellents are not insecticidal. Furthermore, many compositions are either toxic or generally unpleasant to the host. Still others require too many separate active ingredients for efficient production and regulation.

Many synthetic prior art compositions have been proposed as insect repellents, but have later been determined to be unsuitable for safe use by humans. One common active ingredient in prior commercial compositions is N,N-Diethyl-m-toluamide (DEET). However, DEET was subsequently associated with causing various undesirable side-effects, such as stinging, damage to mucous membranes, and possibly seizures. In 1989, the Centers for Disease Control issued a cautionary statement regarding the use of DEET. Many other prior art compounds proposed for use as a repellent have proven unsuitable for topical application to humans or other animals due to their toxic or noxious effect on the infested individual.

Various crude oil extracts of certain plants, such as citronella oil obtained from *Cymbopogon citrata*, or eucalyptus oil obtained from *Eucalyptus citriodora*, have been provided in the prior art as pest repellents. However, the oil complex itself is greasy and may have an unpleasant odor, which makes its use undesirable. Furthermore, consistent production of a safe and effective product is difficult, due to varying amounts of constituent compounds within batches of these complex oils and the difficulty of monitoring a large number of components. Therefore, insect repellents containing the whole oil of citronella, for example, are undesirable due to their limited repellency, unpleasant odor and consistency, and unreliable composition of potentially harmful and unnecessary agents.

Most prior art insect treatments are taught to be effective only with specific synergistic combinations of multiple pesticides. In the art, there has not been recognized a simple but effective pediculicidal and ovicidal composition that is effective and which does not require a combination of excess multiple pesticidal ingredients.

What is needed in the art is an especially effective pediculicidal and ovicidal composition. The composition should also be able to cleanse an individual being treated for infestation.

SUMMARY OF THE INVENTION

The present invention provides a pediculicidal and ovicidal composition containing an active ingredient which demonstrates an extraordinarily lethal effectiveness against parasites, such as lice and their nits. The pediculicidal and ovicidal composition of the present invention is effective in cleansing an individual, human or animal, of a pest infestation.

The composition of the present invention contains an active pediculicidal agent which is at least one purified derivative of an organic oil. These organic oils are typically comprised of a mixture of terpenes. An example of an organic oil from which these compounds can be derived is citronella oil. These purified derivatives can be both pediculicidal and ovicidal. Examples of purified derivatives of citronella oil include citronellal, citronellol and citronellyl based compounds. Purified nerol and geraniol are found in and can also be derived from citronella oil. Another example of an organic oil from which a terpene compound can be derived is teatree oil. Compounds such as terpinen-4-ol and cineole are found in and can be derived from teatree oil. The pediculicidal and ovicidal composition preferably contains an active agent present in a concentration of about 0.1 to 50% w/w. The pediculicidal and ovicidal composition more preferably comprises a citronellyl "salt." The compositions can be administered topically to humans, animals or to any infested areas.

The present invention also includes a method of using the pediculicidal and ovicidal compositions. The method includes applying the composition to the infested area, allowing the composition to remain in contact with the infested area for a period of time, rinsing the composition from the area and, in the case of an infestation of hair such as a lice infestation, combing the infested area with a suitable nit comb.

The method also includes varying the period of time the composition is allowed to remain in contact with the infested area, called the residence or exposure time, so that lower concentrations of active ingredient can be used while pediculicidal and ovicidal effectiveness is maintained. For example, the residence time can be increased when a composition containing a lower concentration of the active ingredient is used in the treatment method.

Therefore, it is an object of the present invention to provide a composition that is mortally effective against parasites, such as lice and their ova.

It is also an object of the present invention to provide an effective pediculicidal and ovicidal composition with lower concentrations of the active ingredient or ingredients that still exhibits pediculicidal and ovicidal activity.

Yet another object of the present invention is to provide a pediculicidal and ovicidal composition capable of cleansing an individual infested with a pest, such as lice.

It is further an object to provide a composition that may be used as a cleansing shampoo, soap, cream, lotion, gel, spray, mousse or powder.

Another object of the present invention is to provide a method of using a pediculicidal and ovicidal composition to cleanse an individual of a pest infestation.

These and other objects of the invention will be apparent to those skilled in the art.

BRIEF DESCRIPTION OF THE DRAWINGS

FIG. 4.a. represents the screening model for 100% pediculicidal activity.

FIG. 4.b. represents the screening model for 100% ovicidal activity prediction profile.

FIG. 4.c. represents the screening model for 100% undeveloped eggs.

FIG. 7.a. shows the mortality rate of one embodiment of the invention.

FIG. 7.b. shows the mortality rate of one embodiment of the invention.

FIG. 7.c. shows the mortality rate of one embodiment of the invention.

DETAILED DESCRIPTION OF THE INVENTION

Figure 1:
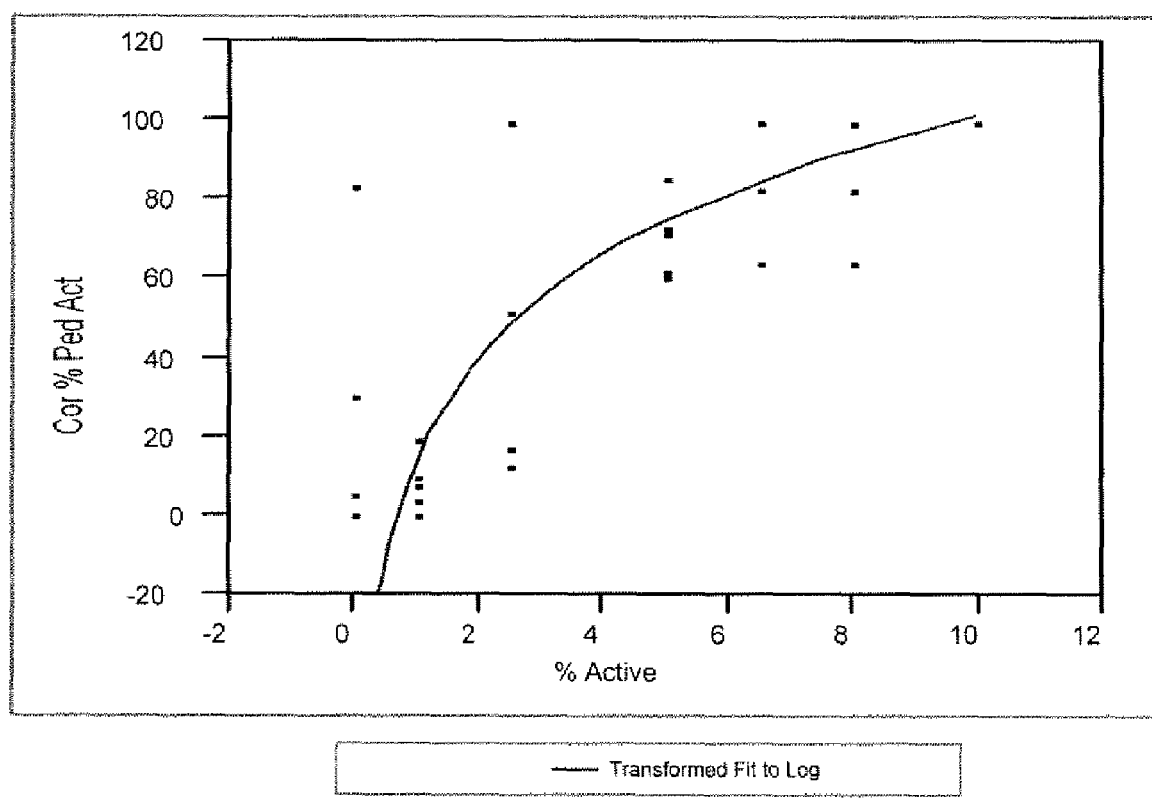
FIG. 1 is the log (ln) fit of the dose response data for pediculicidal activity.

A "pest" is meant to include all parasites, such as but not limited to arthropods, arachnids, triatomes, insects, bugs, flies, lice, fleas, mites, gnats, nits, chiggers, mosquitoes, and ticks, for example. The composition of the present invention is, therefore, intended to be used against all parasites which succumb to the lethal properties thereof.

The present invention provides a pediculicidal and ovicidal composition comprising or consisting essentially of an active purified terpene agent, a short chain organic alcohol, and a component selected from a non-aqueous co-solvent or surfactant, or combinations thereof. The composition can also contain an appropriate viscosity modifier.

The present invention provides pediculicidal and ovicidal compositions comprising an active purified terpene agent. The active agent can be at least one purified derivative of an organic oil. For example, purified derivatives of citronella oil can be used as active agents in pediculicidal and ovicidal compositions. Examples of derivatives purified from citronella oil include citronellal, citronellol and citronellyl compounds. Other examples include nerol and geraniol. Citronellal, citronellol and citronellyl compounds are currently available in the trade as food and cosmetic additives. In preferred embodiments, the pesticidal agent utilized is citronellyl. In preferred embodiments, the citronellyl compound is selected from the group consisting of citronellyl acetate, citronellyl butyrate, citronellyl formate, citronellyl isobutyrate, citronellyl phenylacetate, citronellyl proprionate and citronellyl valerate. In a preferred embodiment, the citronellyl "salt" is the acetate. A highly purified, pharmaceutical grade of citronellyl acetate (approximately 97% pure) may be available from Delmar Chemicals (Montreal, Canada). By "purified" herein is meant that the compound of interest is present in the active agent component of the composition in a purity or quantity at least 75%, 80%, 85%, 90%, 95%, 96%, 97%, 98%, 99% w/w.

The invention preferably provides a pediculicidal and ovicidal composition wherein the active purified terpene agent for example citronellyl, is in a concentration of between about 0.1% and 50%, preferably between about 1% and 40%, preferably between about 2.5% and 30%, preferably between about 5% and 15%, preferably between about 10% and 15% w/w, and preferably about 12.5% w/w.

The compositions also contain a short chain organic alcohol defined as an alcohol having a carbon chain of from 1 to 6 carbon atoms. The short chain alcohol, such as but not limited to ethanol or isopropanol, is incorporated in a concentration of between about 5% and 99.5%, preferably between about 10% and 30% w/w, preferably between about 15% and 25%, and preferably between about 20% w/w.

The compositions also contain a component selected from the group consisting of a non-aqueous co-solvent and a surfactant. The non-aqueous solvent can be selected from compounds such as but not limited to propylene glycol, butylene glycol, polyethylene glycol, hexylene glycol, methoxypolyethylene glycol, or glycerin. The surfactant can be an ionic surfactant, such as but not limited to sodium laureth sulfate (available as STEOL) or sodium lauryl sulfate, or the surfactant can be a non-ionic surfactant such as but not limited to polyoxyethylene sorbitan monolaurate, or polysorbate (available as TWEEN or SPAN), or combinations thereof. This non-aqueous co-solvent and/or surfactant component can be in a concentration of between about 5% and 99.5%, preferably between about 40% and 95%, preferably between about 50% and 90%, preferably between about 55% and 80%, preferably between about 60% and 70%, and preferably about 65% w/w.

The compositions also optionally contain a thickening agent to achieve an effective viscosity, such as described below, such as but not limited to hydroxypropyl celluose (non-ionic), and acrylates/C10-30 alkyl acrylate crosspolymers (ionic) (available as PEMULIN), polyvinylpyrrolidone (PVP), polyvinyl alcohol (PVA) (Carbopol™) and combinations thereof in a concentration of between about 0.01% and 20% w/w, more preferably between about 0.1% and 10% w/w, depending upon the type of thickening agent. A neutralizing agent such as or triethanolamine or sodium hydroxide may also be incorporated for thickening of ionic agents.

Some embodiments of the present invention can also include an anti-oxidant/radical scavenging agent such as but not limited to ascorbic acid (vitamin C) and its salts, tocopherol (vitamin E), and its derivatives such as tocopherol sorbate, other esters of tocopherol, and butylated hydroxy benzoic acids and their salts, such as butyl hydroxytoluene, in order to assist in the removal of pests and their ova. A preferred antioxidant/radical scavenging agent is butyl hydroxytoluene (BHT). The concentration of the antioxidant/radical scavenging agent within the present invention is preferably between about 0.01 and 10% w/w, and preferably between about 0.01 and 4% w/w.

The compositions of the present invention can contain other ingredients so long as the beneficial, pediculicidal and ovicidal nature of the invention is not adversely affected and so long as the effectiveness of the invention is not altered. For example, embodiments of the present invention can contain antimicrobial agents such as methylparaben and propylparaben. Other examples include the addition of a fragrance for aesthetic qualities, addition of propellants for aerosol type formulations, addition of foaming or conditioning agents. Those skilled in the art realize the vast amount of additional excipients that could be added to the formulation for improved aesthetics or delivery of the product to the host.

The composition of the present invention can be used in different forms, such as a liquid body soap or a shampoo. In other embodiments, the present invention takes the form of a gel, an emulsion, a lotion, an aerosol spray, a mousse, or a cream. Preferably, the composition of the present invention is in the form of a surfactant based gel.

The invention also provides a method of treating an individual having a parasite infestation comprising administering to the infestation an insecticide composition as described above. In particular, the composition of the present invention is effective as an insecticide intended for killing and removing lice from humans. Varied treatment regimens are contemplated as being within the method of treatment provided by this invention. Treatment regimens can vary from a single administration to repeated administrations over long time periods. The various possible treatment regimens would be apparent to one skilled in the art based on the invention disclosed herein and are intended to be encompassed in the scope and spirit of the claims.

This method includes applying the composition to the infested area, such as the hair of an individual with a lice infestation. In the case of hair, the composition is left on the hair for a period of time referred to as the residence or exposure time. The residence time can vary as needed to produce effective results. The residence time can be as long as 24 hours and as short as several seconds. Preferably, for the treatment of lice, the residence time is between 1 and 30 minutes. More preferably, the residence time is between approximately 5 and 20 minutes. At the end of the residence time, the composition is rinsed from the area of infestation. These treatment steps of applying and rinsing can be repeated one or more times to complete the removal of the pest infestation. The time period between uses of the pest removing composition can vary as needed to remove the pest infestation from the individual.

Before or after application of the composition the hair may be combed with a suitable nit comb, however combing is not necessarily required. Any suitable nit comb can be used in the described method of use of the composition of the present invention. A suitable nit comb may be made of various materials such as metal and plastic. Metal teeth are sturdier and stiffer than those composed of materials such as plastic. Nit combs with metal teeth therefore often last longer than nit combs without metal teeth. The number of teeth and the diameters of the teeth can also vary. The spacing between teeth can also vary; however, the teeth should be close enough to one another to remove nits. The distance between teeth should be 0.3 mm or less, the generally accepted width of nits attached to human hair. Preferably, a nit comb such as the ALB006 is used, which is available from Albyn Stonehaven Ltd. (Stonehaven, Scotland). This comb has 62 metal pins arranged side by side which act as the teeth of the comb. These pins extend approximately 12.5 mm from a plastic piece which acts as the handle of the nit comb. The pins on either end have a diameter of 0.9 mm and the 60 inner teeth have a diameter of 0.6 mm. The gap between the teeth is 0.3 mm.

To the inventors' knowledge, there has not previously been a recognition of the pediculicidal and ovicidal effectiveness of the present compositions containing active purified terpene agents such as citronellyl, citronellal, citronellol, nerol or geranol that possess a surprising degree of pediculicidal and ovicidal effectiveness in combination with the short-chain alcohol, other non-aqueous co-solvents and/or surfactants and optionally an appropriate viscosity modifier. It is surprising that other detergents, such as aqueous detergents, or acids, such as acetic acid (in concentrations of greater than 5%), are not required in the invention. It is noted that propylene carbonate is not a necessary ingredient to provide the observed synergistic effect of the invention. Additionally, to the inventors' knowledge, there has not been a previous recognition or demonstration of the effectiveness of the present invention at cleansing individuals of pest infestations. One skilled in the art can routinely modify the relative concentrations of these components, and accordingly the ratio of their combination, to yield a functional pesticide composition.

Without being limited by theory, it is believed that the composition of the present invention is surprisingly effective due in part to the purification of individual compounds. Citronella oil is a complex mixture containing components which may ordinarily mask the potential effectiveness of the individual purified terpene pesticidal agents, such as citronellyl, citronellol, and citronellal, as disclosed by the present invention. It also appears that a synergistically beneficial effect is achieved in the compositions of the present invention.

The present invention is intended to be administered topically to infested areas of an individual, such as the hair and scalp or pubic areas. The composition is preferably provided in the form of a liquid or solid, such as shampoo, soap, cream, or lotion. The invention contemplates that various other complimentary ingredients can be included, such as an antipruritic agent, a pH modifier, or as a general medium. For example, glycerins, glycols, alcohols, lanolins, aloe vera gel, may be provided in the composition. The preferred compositions are shampoos and soaps containing ingredients capable of assisting in cleansing individuals of the debris of dead parasites.

The composition may also be provided in sun screening, tanning or any other topically applicable products. Other uses of the composition are contemplated, such as a pediculicidal and ovicidal spray or logger for application directly to pests or potentially infested areas. For example, the composition can be provided as a pesticide and cleaning agent for fruits and vegetables. The composition can additionally serve as a parasite repellent for humans, cats, dogs, birds, cattle, or sheep, for example. The composition may also be used as a carpet powder, or as a detergent additive, rinse or spray for clothing, bedding or other fabrics. The composition may also be used as an aerosol bomb or as a room spray. Other such uses would be apparent to one skilled in the art upon contemplating the invention disclosed herein and such uses are intended to be encompassed in the scope and spirit of the claims.

EXAMPLES

Summary of New In Vitro Assessments Developed

Currently, the most widely used in vitro methods used to assess the insecticidal qualities of a lice treatment product or compound are ASTM methods E 938-83, "Standard Test Method for Effectiveness of Liquid, Gel, or Cream Insecticides Against Adult Human Lice," and E 1517-93, "Standard Test Method for Determining the Effectiveness of a Liquid, Gel, Cream, or Shampoo Insecticides Against Human Louse Ova."

For these methods, a strain of human body lice has been adapted to feed on rabbit blood. The current ASTM tests are used early in the development process for initial pre-clinical assessments of possible lice treatments. Also, these tests are sometimes used to "substantiate" marketing claims of pediculicidal and/or ovicidal activity. Poor correlation between the in vitro results and in vivo efficacy may be seen especially for ovicidal assessments.

Therefore, a need existed to develop new in vitro methods that incorporate different application and assessment techniques. Incorporation of the new techniques hopefully would result in a better correlation between the methods for adequate prediction of in vivo activity and future product success.

Two main critical differences exist between the in vitro and in vivo methods that could lead to the limitations. First, the in vitro test incorporates human body lice that have been adapted to feed on rabbit blood not human head lice, which feed on human blood. It is plausible that a difference in efficacy could be observed based on the difference in species being tested. Second, in the in vitro tests, lice or nits being treated are completely submerged in the test solution for the entire identified residence time. This method of "application" of the product is drastically different than topical application in vivo. A similar in vivo application would be to submerge a child's hair in the test product. This is obviously not the most practical or safe method of actual application.

This "first scenario" (difference in species) was initially investigated. The ASTM ovicidal assessment test was duplicated in the field using human head lice nits attached to hair. The hair was clipped with the attached nit and treated identically according to the ASTM method. No statistically significant difference in efficacy was observed. This indicates that good correlation exists between using the adapted strain of human body lice ova versus actual human head lice ova. Therefore, efforts were focused onto the application and assessment techniques.

Since submersion would never be a justified application technique in vivo, the application aspect of the pediculicidal assessment was amended. Instead of submerging the lice in the product for the entire residence time, the lice were allow to crawl on a small piece of gauze and then submerge in the test product for 5 seconds. They were then removed and placed in an empty petri dish where they remained undisturbed for the remainder of the identified residence time. Obviously, this application procedure is much more indicative of in vivo application where the product is applied from the bottle in a large quantity, worked into the hair (thinning effect), and allowed to sit for the identified time.

Assessment of the new application technique was performed with the critical strength of citronellyl acetate (in original vehicle) previously identified using the original ASTM method. The original method showed that when 5.0, 7.5, 10.0, and 12.5% citronellyl acetate were tested that 5.0% was the critical strength as it was the only strength not to exhibit 100% activity (actually was 91.9%). When tested with the new application technique, the 5.0% strength possessed only 62.3%. This indicates that the new method with the different application technique is much more rigorous or may help to explain the lack of 100% in vivo efficacy.

The application technique for the in vitro ovicidal test method was also amended. In the ASTM method, adult lice were allowed to lay eggs on clipped human hair. Then, ten hair strands, 1 nit attached to each, were taped to an applicator stick. Finally, the applicator stick with hair and nits was submerged in the test solution for the entire identified residence time. The new application method incorporated "tresses" of hair. Each tress was a collection of human hair bundled at one end, and the lice were allowed to lay numerous eggs on these tresses (about 200-300 nits per tress). The tresses were woven into sections of a human hair wig, and the wig was secured to a non-porous solid surface "head." The test product and a control (water) was applied each section of the wig with a method similar to typical shampooing or applying a cream rinse in under 2 minutes. After application, the product was allowed to remain, undisturbed, in contact for the identified residence time. After the residence time, the wig was rinsed thoroughly (until no visible signs of product remained) with tap water and towel dried. The tresses, with nits, were removed from the wig and incubated under appropriate conditions for 14 days post treatment.

In addition to the new application technique, new assessments were also included in the new in vitro ovicidal study. These new assessments were incorporated in an effort to determine the level of the products penetration through the various protective structures of the nit. In theory, these additional assessments would provide much better evaluation of a product's ability to penetrate and potential in vivo ovicidal activity. The two new assessments were determination of level of hatching (ie: "half-hatched") and "eye spot formation"

Level of hatching is basically a "pass/fail" assessment of penetration. For example, if the product penetrates the nit pore but not the nit membrane (used for regulation of gas transport), the product will collect around the membrane (common with currently marketed products). Therefore, the nit will actually develop and begin to hatch. However, once the nymph has broken the membrane, it is exposed to a certain level of active. If enough active is present, it will kill the nymph while hatching, and this can be documented as a "half hatched" nit. If the nit is exposed but not killed, it could become resistant to future treatment with the compound. This could be one explanation of the documented resistance of human head lice to current actives.

Assessment and location of eye spot formation provides a more detailed measurement of penetration. At the time of treatment, the nits have not developed eyespots. Therefore, if the product completely penetrates inside the nit, it will be killed at the time of exposure and no development will occur. However, if eyespot formation is seen it indicates lack of penetration, and the location of the eyespot can even predict the level of penetration.

Finally, the two additional assessments were used to tabulate "% Undeveloped" nits. Nits that showed no signs of development (i.e. excludes nits that were half hatched or had eye spot formation) were tabulated. The number of undeveloped nits was divided by the total number of nits treated and multiplied by 100 for reporting "% Undeveloped."

A vehicle with 10.0% and 12.5% strengths of citronellyl acetate was used to assess the ovicidal activity with the new method. The ASTM method resulted in 100% activity for both strengths. While the new method resulted in 96.2% and 98.1% activity respectively, only 53.4% and 72.0% of the nits were undeveloped respectively. Obviously, the new method shows that while the overall effect may be positive (i.e. almost 100%) the underlying ability of the product to penetrate may not correlate with the activity. This study was carried out in a controlled manner and still resulted in nit development. This can easily explain the lack of ovicidal activity in less controlled in vivo studies.

As the new methods clearly are better tools for assessment, they were used for all future in vitro formulation assessments.
Summary of Formulations Developed and Hypotheses Involved Previous development work of a lice treatment product incorporating citronellyl acetate as an active ingredient resulted in a product that consisted of two separate components. The components had to be mixed just prior to use due to a lack of product stability upon mixing. This two-component product could result in improper use or mixing (human error), more potential for side effects, less patient compliance, and less willingness to use the product. Also, the formulation incorporated acetic acid and proved to cause considerable dermal irritation (PDI testing of the two-component formulation after mixing resulted in a score of 6.75, a severe irritant).

Therefore, a considerable amount of research was initiated to develop a product that would be less irritating, even more active, and could be packaged in a single container. First attempts to overcome these issues resulted in an "anhydrous" formulation. The formulation was an oil-in-water (O/W) emulsion (instead of a solution, original two-component formulation) and is referenced in U.S. Pat. No. 5,902,595. The product was designed as a cream rinse incorporating conditioners in lieu of the surfactant, sodium laureth sulfate. For irritation issues, it was believed that the conditioner might soothe the irritating effects. For stability issues, it was hypothesized that by emulsifying the citronellyl acetate (an oil), it would be protected from the acid degradation process and oxidation resulting in a significant increase in stability for the single component formulation. Following is a summary of that formulation:

| Ingredient | % (w/w) |
| --- | --- |
| IPA | 20.0 |
| Acetic Acid | 5.0 |
| Cedepal HC | 15.0 |
| Propylene Glycol | 20.0 |
| Glycerin | Diluent |
| Methylparaben | 0.2 |
| Propylparaben | 0.1 |
| Citronellyl Acetate | 12.5 |

However, in vitro testing revealed that while this formulation was pediculicidal (99.8%) it possessed no ovicidal activity (1.6%). Due to the lack of in vitro ovicidal efficacy, additional emulsified formulations were developed in attempt to incorporate the sodium laureth sulfate and acetic acid into a single component. The theory was that in an O/W emulsion, citronellyl acetate (an oil) would be protected from the acetic acid (soluble in the water phase). The protection from acid degradation would result in increased stability. Many O/W formulations were developed consisting of various types of emulsifiers.

In addition, efforts were focused on increasing viscosity according to the hypothesis that increasing the viscosity of the formulations would increase stability (increasing viscosity will slow down collisions) and efficacy (increase contact time with pest). Theoretically, increasing the viscosity of the formulation will impede molecular motion and slow down particle collisions, directly affecting the degradation kinetics and slowing the decomposition of the active ingredient. Also, increasing viscosity would increase the contact time and decrease evaporation of the active ingredient while on the pest. This would result in the pest being exposed to more active ingredient for longer durations of time, directly increasing efficacy.

Various different O/W formulations were developed in attempt to increase the viscosity of the overall product. Most of these formulations incorporated the same ingredients as the original formulation (citronellyl acetate, IPA, acetic acid, methylparaben, and propylparaben). However, for formulation of a thicker emulsion, mineral oil and thickening, emulsifying agents were substituted in lieu of a surfactant. Examples of thickening, emulsifying agents incorporated into the formulation are various grades of Carbopol™ (carbomer), PVP (polyvinylpyrrolidone), Pemulen® (Acrylates/C10-30 Alkyl Acrylate Crosspoly-mer), Klucel HF® (hyroxypropyl cellulose), hydroxyethtyl cellulose, hydroxypropylmethyl cellulose, and each was used individually and in combination with the others. Also, buffer systems (such as sodium acetate trihydrate) and neutralizing agents (such as TEA, triethanolamine) were included as needed. Following is a table summarizing the ingredients and ranges used in the most desired O/W emulsions developed.

| Ingredient | % (w/w) |
| --- | --- |
| IPA | 20.0 |
| Acetic Acid | 5.0 |
| Purified water | 59.1-60.8 |
| Pemulen ® TR-1 | 1.75-3.50 |
| Citronellyl Acetate | 10.0 |
| Methylparaben | 0.0-0.2 |
| Propylparaben | 0.0-0.1 |
| Mineral Oil | 2.0 |

One specific formulation (included in above ranges with 1.75% Pemulen® TR-1) was tested for stability and in vitro pediculicidal efficacy. This formulation resulted in much greater stability as a single component but in vitro pediculicidal testing indicated poor efficacy.

Because a lack of efficacy existed while still incorporating acetic acid, focus was shifted on developing a single component, acid free, clear gel formulation. Clear gel formulations offer many positive attributes. First, they are typically thickened alcoholic solutions. This allows for greater drug uniformity, greater drug loading, greater contact time, and less phase separation. Also, topical gels can incorporate non-aqueous solvents such as glycerin and propylene glycol that also can enhance penetration and possess humectant qualities, which can increase the penetration of the active and help to overcome any irritating effects of other ingredients.

These new formulations incorporated an antiparasitic compound, citronellyl acetate, as the active purified terpene agent, but citronellol, citronellal, gerianol, and/or nerol can also be used, for example. A short chain organic alcohol was included as a solvent and was used as the diluent. Specific examples of alcohol used are isopropyl alcohol and ethanol. Other non-aqueous solvents were included such as propylene glycol and glycerin. Other anhydrous glycols such as butylene glycol, hexylene glycol, polyethylene glycol, methoxypolyethylene glycol, and their derivatives could be included. Also to stabilize the formulation, an antioxidant/radical scavenging agent, butyl hydroxytoluene (BHT), was incorporated. Also, chelating agents can be added to improve stability since they form complexes with metal ions rendering them unavailable for reaction and/or as a catalyst for other reactions, which usually results in increased stability of the formulation. An example of a possible chelator is EDTA. Antimicrobial preservatives, methylparaben and propylparaben, were included and are commonly used for inhibition of microbial growth in liquid or semi-solid formulations. Other examples of common preservatives are benzoic acid, sodium benzoate, and benzalkonium chloride (BAK).

Some of the new formulations were thickened with alcohol compatible polymers such as hydroxypropyl cellulose (HPC, "Klucel® HF), polyvinylpyrrolidone (PVP), and Pemulen TR-1® and TR-2® (CTFA name: Acrylates/C10-30 Alkyl Acrylate Crosspolymer), hydroxyethyl cellulose, and hydroxymethylpropyl cellulose. Various amounts of the thickeners were added to optimize the viscosity of the formulation. In theory, this would increase the contact time of the active ingredient with the pest and decrease side effects such as burning of the eyes and mucous membranes (due to a thin product running off the hair and onto the face and eyes).

The following two tables summarize some of the single component, acid free, o/w emulsion and clear gel formulations developed and various methods used to manufacture the product:

| Ingredient | Ranges developed (% w/w) |
|---|---|
| IPA | 0.0-58.45 |
| Ethanol (95%) | 0.0-51.95 |
| BHT | 0.05 |
| Propylene Glycol | 10.0-20.0 |
| Glycerin | 10.0-20.0 |
| Klucel HF ® (HPC) | 0.0-2.0 |
| Pemulen TR1 | 0.0-3.0 |
| Citronellyl Acetate | 0.5-8.0 |

| Ingredient | % (w/w) |
|---|---|
| Citronellyl acetate | 8.0, 10.0, 12.5 |
| Methylparaben | 0.0, 0.2 |
| Propylparaben | 0.0, 0.1 |
| PVP | 0.0, 1.0 |
| Pemulen ® | 0.25-2.5 |
| Glacial Acetic Acid | 0.0, 5.0 |
| IPA | 20.00 |
| Sodium Laureth Sulfate (25%) | 0.0, 50.0 |
| TEA | 0.0, 0.4 |
| Sodium Hydroxide | 0.0-1.0 |
| Purified Water | diluent |

Preparation of Thickened Existing Acetic Acid Formulations without Neutralizer

| Step | Description |
|---|---|
| 1 | Add alcohol to an adequately sized mixing vessel (#1) and begin mixing |
| 2 | While mixing, add methylparaben and propylparaben and mix until completely dissolved |
| 3 | While mixing, add citronellyl acetate, then Steol CS-230, then purified water mixing for 2 minutes after each addition |
| 4 | Heat the solution from step #3 to 40-45° C. |
| 5 | Add Pemulen to the hot solution from step #4 and mix well while maintaining the temperature at 40-45° C. until completely hydrated |
| 6 | Cool to room temperature (about 25° C.) |

First Preparation of o/w Emulsion Formulations without Neutralizer

| Step | Description |
|---|---|
| 1 | Add citronellyl acetate and mineral oil to an adequately sized mixing vessel (#1), begin mixing, and heat to 60-65° C. |
| 2 | While mixing and maintaining the temperature at 60-65° C., add Pemulen and mix until well dispersed |
| 3 | In a separate, adequately sized vessel (#2), mix water and alcohol and heat to 50-55° C. |
| 4 | While mixing and maintaining the temperature at 50-55° C., disperse the PVP in the solution from step #3 (in vessel #2) and continue mixing until the PVP is well hydrated |
| 5 | Add glacial acetic acid to the hot solution from step #4 (vessel #2) and mix well while maintaining the temperature at 50-55° C. |
| 6 | While mixing and maintaining the temperature at 50-55° C., add the solution in vessel #1 to that in vessel #2 and mix until completely uniform |
| 7 | Cool to room temperature (about 25° C.) |

Second Preparation of o/w Emulsion Formulations without Neutralizer

| Step | Description |
|---|---|
| 1 | Add water, alcohol, and acetic acid to an adequately sized mixing vessel (#1), begin mixing, and heat to 40-50° C. |
| 2 | While mixing and maintaining the temperature at 60-65° C., add methylparaben and propylparaben and mix until completely dissolved |
| 3 | While mixing and maintaining the temperature at 40-50° C., disperse the PVP in the solution from step #2 (in vessel #1) and continue mixing until the PVP is well hydrated |
| 4 | Add citronellyl acetate and mineral oil to a separate, adequately sized mixing vessel (#2), begin mixing, and heat to 60-65° C. |
| 5 | Add Pemulen to the hot solution from step #4 (vessel #2) and mix well while maintaining the temperature at 40-50° C. until completely hydrated |
| 6 | While mixing and maintaining the temperature at 50-55° C., add the solution in vessel #1 to that in vessel #2 and mix until completely uniform |
| 7 | Cool to room temperature (about 25° C.) |

Third Preparation of o/w Emulsion Formulations without Neutralizer

| Step | Description |
|---|---|
| 1 | Add water, alcohol, and acetic acid to an adequately sized mixing vessel (#1) and mix for 2 minutes |
| 2 | While mixing, add methylparaben and propylparaben, begin heating the solution to 40-50° C., and mix until completely dissolved |
| 3 | While mixing and maintaining the temperature at 40-50° C., disperse the PVP in the solution from step #2 and continue mixing until the PVP is well hydrated |
| 4 | In a separate, adequately sized mixing vessel (#2), add citronellyl acetate and mineral oil, begin mixing, and heat to 35-45° C. |
| 5 | While mixing and maintaining temperature at 40-50° C., add the contents of vessel #2 to that in vessel #1 |
| 6 | Add Pemulen to the hot solution from step #5 and mix well while maintaining the temperature at 40-50° C. until completely hydrated |
| 7 | Cool to room temperature (about 25° C.) |

Preparation of o/w Emulsion Formulations with Neutralizer

| Step | Description |
|---|---|
| 1 | Add citronellyl acetate and mineral oil to an adequately sized mixing vessel (#1), begin mixing, and heat to 60-65° C. |
| 2 | While mixing and maintaining the temperature at 60-65° C., add Pemulen and mix until well dispersed |
| 3 | In a separate, adequately sized vessel (#2), mix water and alcohol, and heat to 50-55° C. |
| 4 | While mixing and maintaining the temperature at 50-55° C., disperse the PVP in the solution from step #3 (in vessel #2), and continue mixing until the PVP is well hydrated |
| 5 | Add neutralizer (TEA or NaOH) to the hot solution from step #4 (vessel #2) and mix well |
| 6 | While mixing and maintaining the temperature at 50-55° C., add the solution in vessel #1 to that in vessel #2, and mix until completely uniform |
| 7 | Cool to room temperature (about 25° C.) |

Preparation of Clear Gel Formula

| Step | Description |
|---|---|
| 1 | Add alcohol to an adequately sized mixing vessel (#1) and begin mixing |
| 2 | While mixing, add BHT and mix until completely dissolved |
| 3 | While mixing, add propylene carbonate, then propylene glycol, and then glycerin mixing for 2 minutes after each addition |
| 4 | While mixing, slowly add Klucel (or other type of thickener) and mix until completely hydrated and a uniform gel is achieved |

Five specific formulations were developed that possessed the best aesthetic qualities and could be tested for the effect of the alcohol selection and viscosity. In general two thin (water like) formulations were made, 1 with ethanol and the other with IPA. The third formulation incorporated ethanol and Klucel® HF as a thickener (resulted in molasses type consistency). Each was tested for in vitro efficacy. Following are the three formulations and in vitro test results:

Formulation 022800-006A:

| Ingredient | % w/w |
|---|---|
| IPA | 51.95 |
| BHT | 0.05 |
| Propylene Glycol | 20.0 |
| Glycerin | 20.0 |
| Citronellyl Acetate | 8.0 |

Formulation 022800-007A:

| Ingredient | Ranges developed (% w/w) |
|---|---|
| Ethanol (95%) | 51.95 |
| BHT | 0.05 |
| Propylene Glycol | 20.0 |
| Glycerin | 20.0 |
| Citronellyl Acetate | 8.0 |

Formulation 022800-007B:

| Ingredient | Ranges developed (% w/w) |
|---|---|
| Ethanol (95%) | 50.95 |
| BHT | 0.05 |
| Klucel HF ® | 1.0 |
| Propylene Glycol | 20.0 |
| Glycerin | 20.0 |
| Citronellyl Acetate | 8.0 |

In Vitro Data

| Formulation | % Pediculicidal Activity | % Ovicidal Activity | % Undeveloped |
|---|---|---|---|
| 006A | 80.3 | 99.2 | 98.1 |
| 007A | 41.7 | Not Tested | Not Tested |
| 007B | 88.9 | 100 | 99.5 |

The testing shows a twofold increase in pediculicidal effectiveness when IPA is used instead of ethanol (006A vs. 007A). Also, a twofold increase in effectiveness is seen when the thin ethanol formulation is thickened (007A vs. 00713). However, both the thin IPA formulation and the thickened ethanol formulation are ovicidal and result in basically no development of the nit after exposure. Surprisingly, acetic acid was not required to achieve successful ovicidal activity. Inclusion of propylene carbonate had absolutely no effect on the efficacy of the formulations. The in vitro data indicates that an optimized formulation would incorporate IPA as the alcohol, should be thickened, and would not need to incorporate propylene carbonate.

Therefore, additional formulations were developed and tested. The first additional formulations were hybrids of 006A and 007B incorporating IPA as the alcohol and Klucel® HF for thickening. A series of the vehicle were made with decreasing amounts of citronellyl acetate. Also, in other formulations, Pemulen TR-1® was incorporated in lieu of Klucel® HF to assess the effect of thickener used. These formulations were tested for in vitro efficacy, and following is a summary of the formulations and in vitro pediculicidal activity:

| Ingredient | 041100-002A | 041100-003A | 041100-004A | 041100-004B | 041800-005A | 041800-006A | 041800-007A |
|---|---|---|---|---|---|---|---|
| IPA | 53.95% | 56.45% | 57.95% | 58.45% | 53.45% | 48.95% | 49.95% |
| BHT | 0.05% | 0.05% | 0.05% | 0.05% | 0.05% | 0.05% | 0.05% |
| Propylene Glycol | 20.00% | 20.00% | 20.00% | 20.00% | 19.70% | 20.00% | 20.00% |
| Glycerin | 20.00% | 20.00% | 20.00% | 20.00% | 19.80% | 20.00% | 20.00% |
| Propylene Carbonate | | | | | | | |
| Klucel HF ® (HPC) | 1.00% | 1.00% | 1.00% | 1.00% | | | |
| Pemulen ® TR1 | | | | | 2.00% | 3.00% | 2.00% |
| Citronellyl Acetate | 5.00% | 2.50% | 1.00% | 0.50% | 5.00% | 8.00% | 8.00% |
| % Pediculicidal Activity | 79.7 | 93.1 | 42.9 | 67.2 | 74.6 | 100 | 100 |

The data indicates that neither the type of thickener nor minor viscosity differences affect the efficacy as long as the final product is produced from a solution that is thickened to form a clear gel.

While fairly high levels of Pemulen® were required to reach the desired consistency, it should be noted that the amount of Pemulen TR-1® and TR-2® required for thickening the formulation could be greatly reduced by adding a small amount of a neutralizing agent. These neutralizers could be any strong or weak bases, and specific examples are sodium hydroxide, triethanolamine (TEA), and aminomethyl propanol. If the concentration of alcohol is greater than 50%, a more alcohol soluble amine may be required. Specific examples are Quadrol® or Neutrol® (tetra-2-hydroxypropyl ethylene diamine), Ethomeen® C-25 (PEG 15 Cocamine), DPA (diisopropylamine), or AMP (amino methyl propanol). Following is an example of one formulation developed that incorporated less thickener and a neutralizer:

| Ingredient | 113000-044A |
|---|---|
| IPA | 15.0% |
| BHT | 0.05% |
| Propylene Glycol | 75.06% |
| Citronellyl Acetate | 10.00% |
| Pemulen ® TR1 | 0.85% |
| Sodium Hydroxide | 0.04% |

A series of formulations were prepared with various concentrations of IPA and were tested for in vitro pediculicidal and ovicidal efficacy (wig method). All of the formulations incorporated 8.0% citronellyl acetate and were identical with the exception of alcohol concentration. Due to the minimization efforts, propylene glycol was used as the diluent instead of the alcohol. Following is a summary of the formulations prepared and their corresponding activities:

| Ingredient | % (w/w) | | | | |
|---|---|---|---|---|---|
| IPA | 10.00 | 20.00 | 30.00 | 40.00 | Control |
| BHT | 0.05 | 0.05 | 0.05 | 0.05 | — |
| Propylene glycol | 59.95 | 49.95 | 39.95 | 29.95 | — |
| Glycerin | 20.00 | 20.00 | 20.00 | 20.00 | — |
| Pemulen ® TR1 | 2.00 | 2.00 | 2.00 | 2.00 | — |
| Citronellyl acetate | 8.00 | 8.00 | 8.00 | 8.00 | — |
| % Ped. Act. | 100.0 | 100.0 | 100.0 | 100.0 | 12.0 |
| % Ovicidal Act. | 100.0 | 100.0 | 100.0 | 99.5 | 10.2 |
| % Undeveloped Eggs | 99.5 | 99.8 | 98.0 | 98.0 | 53 |

As evident from the study, activity was not related to the IPA concentration.

A series of formulations were also prepared for an in vitro dose response study. The dose response study was designed by formulating the clear gel vehicle with 10% IPA and various levels of citronellyl acetate between 0.0 to 10.0%. The formulations were assessed for in vitro pediculicidal activity using the modified methods previously described. All formulations possessed viscosities between 1500-3000 cps, and following is a summary of the clear gel formulations that were prepared for the dose response study and the resulting data from the assessments:

| Ingredient | % (w/w) | | | | | | |
|---|---|---|---|---|---|---|---|
| IPA | 10.00 | 10.00 | 10.00 | 10.00 | 10.00 | 10.00 | 10.00 |
| BHT | 0.05 | 0.05 | 0.05 | 0.05 | 0.05 | 0.05 | 0.05 |
| Propylene glycol | 67.95 | 66.95 | 65.45 | 62.95 | 61.45 | 59.95 | 57.95 |
| Glycerin | 20.00 | 20.00 | 20.00 | 20.00 | 20.00 | 20.00 | 20.00 |
| Pemulen ® TR1 | 2.00 | 2.00 | 2.00 | 2.00 | 2.00 | 2.00 | 2.00 |
| Citronellyl acetate | 0.00 | 1.00 | 2.50 | 5.00 | 6.50 | 8.00 | 10.00 |
| % Killed | 14.9 | 5.1 | 28.7 | 25.0 | 81.2 | 97.9 | 99.0 |
| % Corrected Ped. Act. | 21.3 | 6.7 | 54.2 | 59.7 | 89.4 | 100 | 100 |
| % Undev'd Eggs | 16.4 | 21.3 | 12.0 | 98.3 | 74.2 | 85.9 | 65.5 |
| Corrected % Ovicidal Act. | 1.1 | 37.7 | 37.8 | 100 | 84.2 | 98.5 | 97.9 |

An ANOVA analysis was performed (with $\alpha=0.025$) to determine statistically significant activity above that of the water control (p-values>$\alpha$ indicate no significant activity). Following were the results of the analysis:

| | Data Analyzed | | |
|---|---|---|---|
| Strength | % Ped. Act. p-value | % Ovicidal Act. p-value | % Undev'd Eggs p-value |
| Vehicle | 0.324999 | 0.992901 | 0.228258 |
| 1.0% | 0.759547 | 0.045519 | 0.038553 |
| 2.5% | 0.03279 | 0.004057 | 0.259956 |
| 5.0% | $1.5 \times 10^{-6}$ | $4.8 \times 10^{-5}$ | $1.2 \times 10^{-5}$ |
| 6.5% | $4.2 \times 10^{-6}$ | 0.001045 | 0.001009 |
| 8.0% | $4.2 \times 10^{-6}$ | $4.8 \times 10^{-6}$ | 0.000412 |
| 10.0% | $2.1 \times 10^{-10}$ | $6.1 \times 10^{-5}$ | 0.000118 |

The ANOVA analysis identified that products incorporating greater than 2.5% citronellyl acetate are capable of statistically significant pediculicidal activity and a statistically significant number of eggs remaining undeveloped. It also identified that products incorporating greater than 1.0% were capable of statistically significant ovicidal activity.

Figure 2:
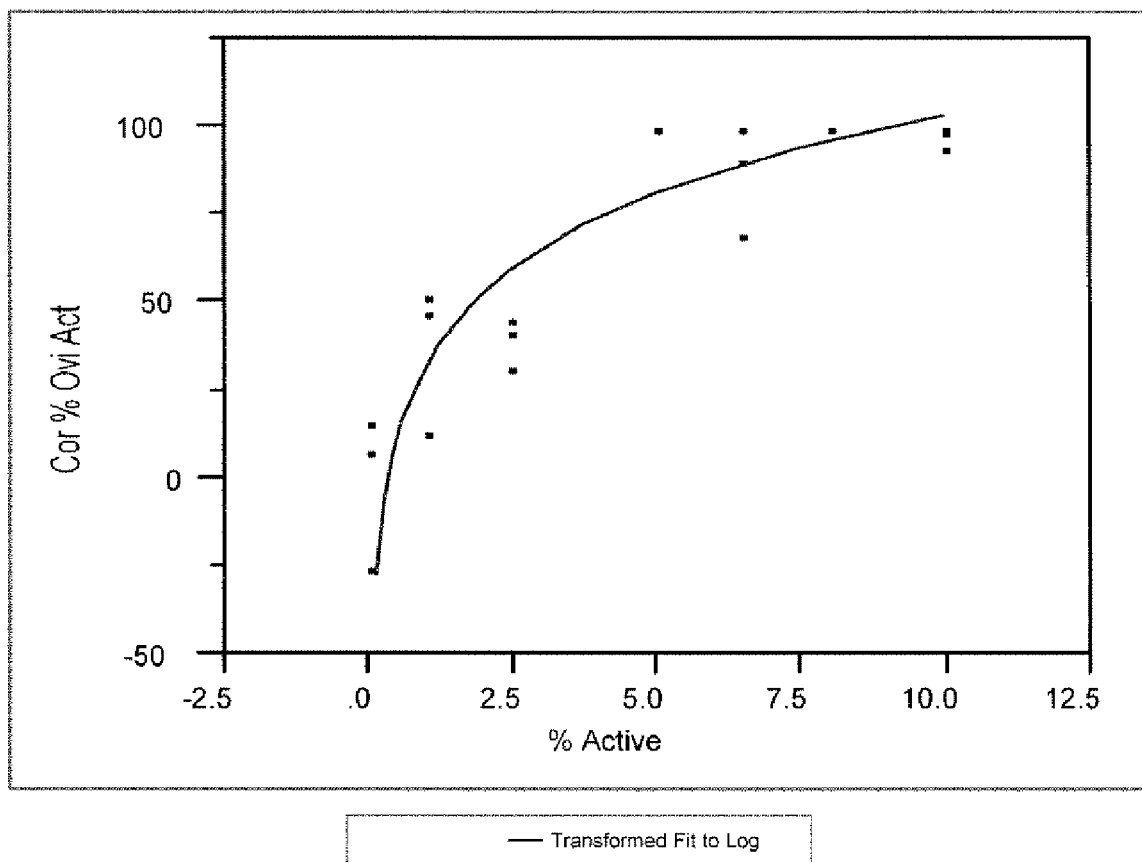
FIG. 2 is the log (ln) fit of the dose response data for ovicidal activity.
Figure 3:
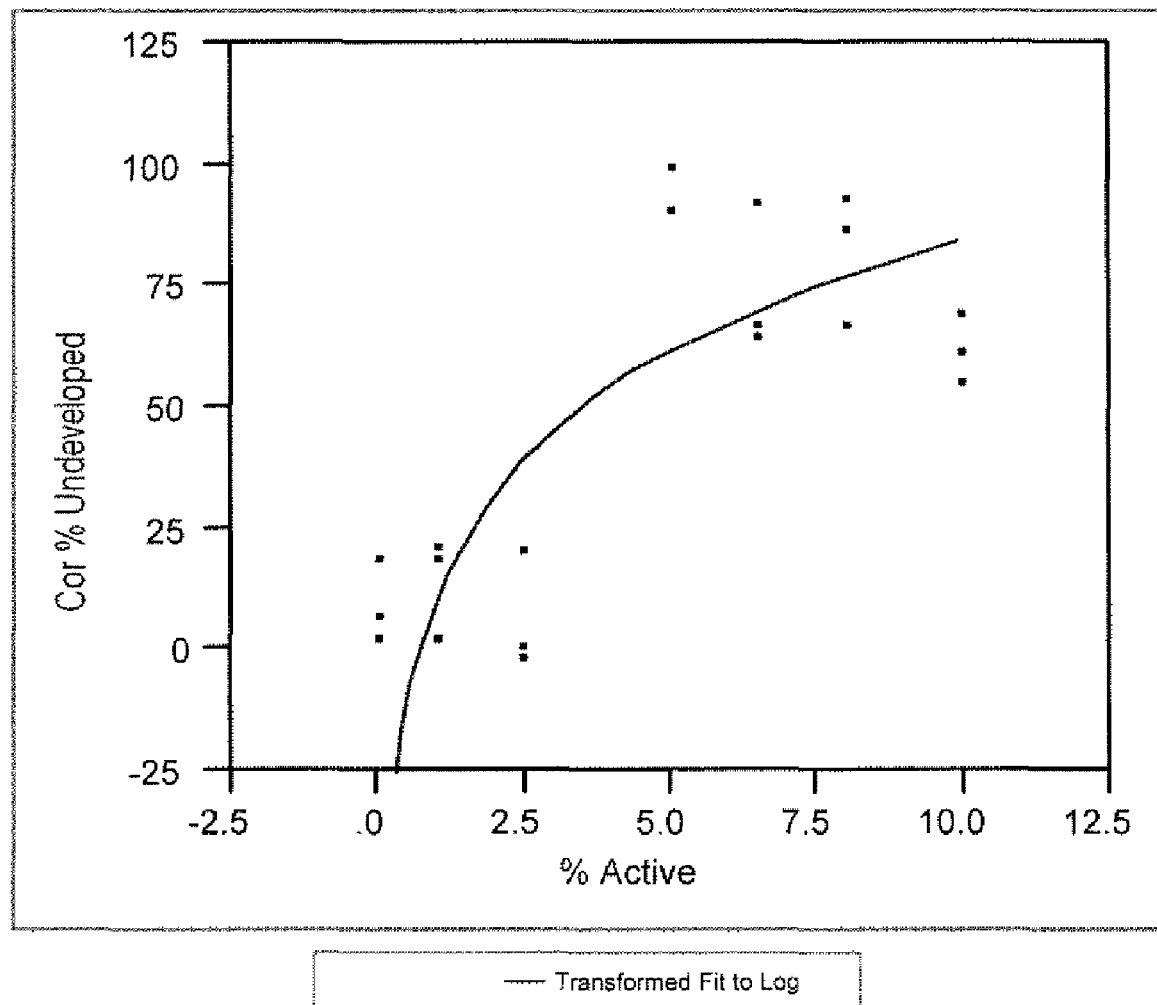
FIG. 3 is the log (ln) fit of the dose response data for undeveloped eggs.

The resulting data for pediculicidal activity (FIG. 1), ovicidal activity (FIG. 2), and for undeveloped eggs (FIG. 3) was statistically modeled using a log (ln) fit of the data typical of that observed with dose response data. In addition, a screening model was used to identify the minimum dose predicted to elucidate 100% pediculicidal activity in vitro (FIG. 4.a.), 100% ovicidal activity in vitro (FIG. 4.b.), and 100% undeveloped eggs in vitro (FIG. 4.c.).

Figure 5:
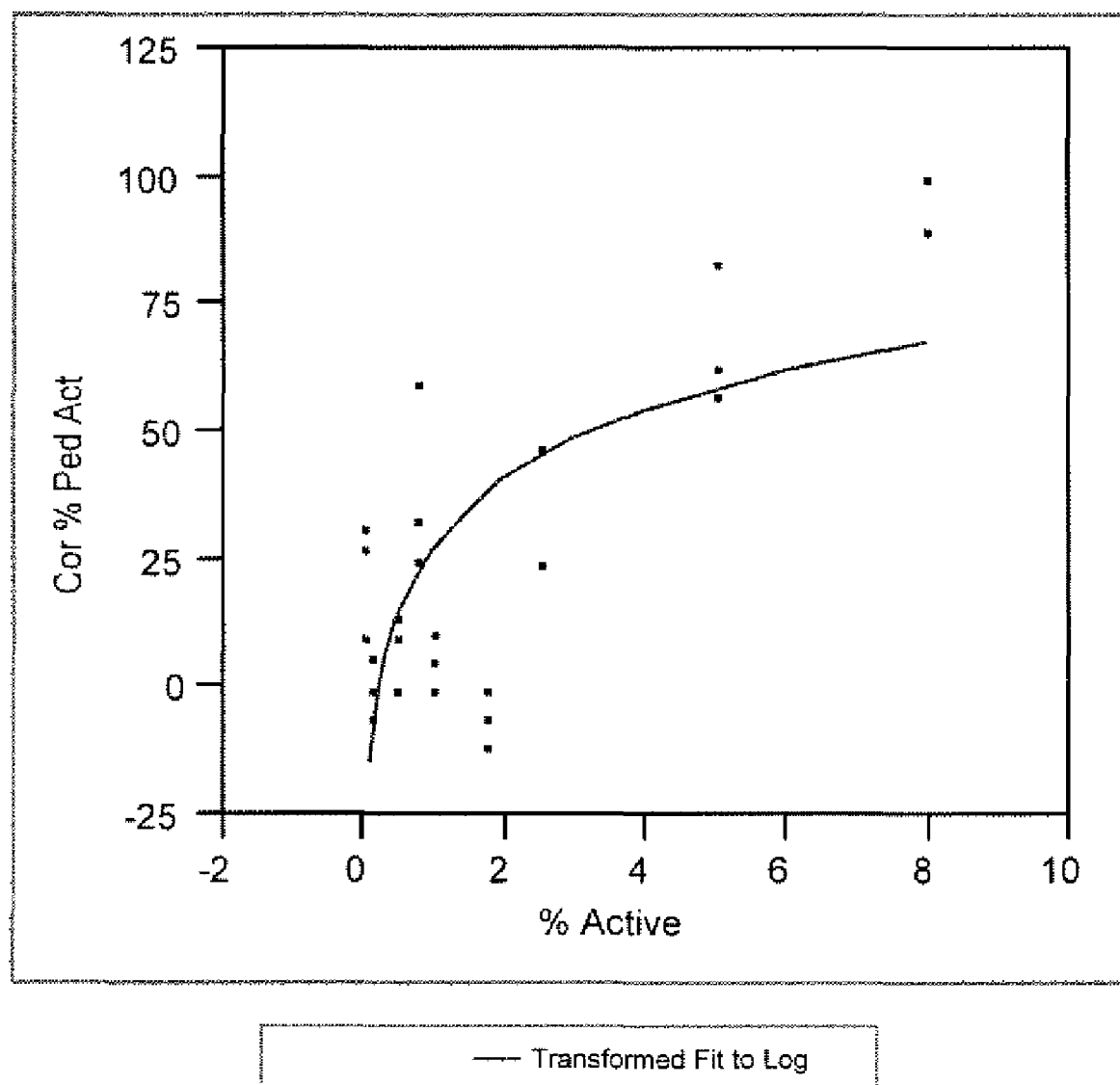
FIG. 5 is the log (ln) fit of the prior art dose response data for pediculicidal activity.
Figure 6:
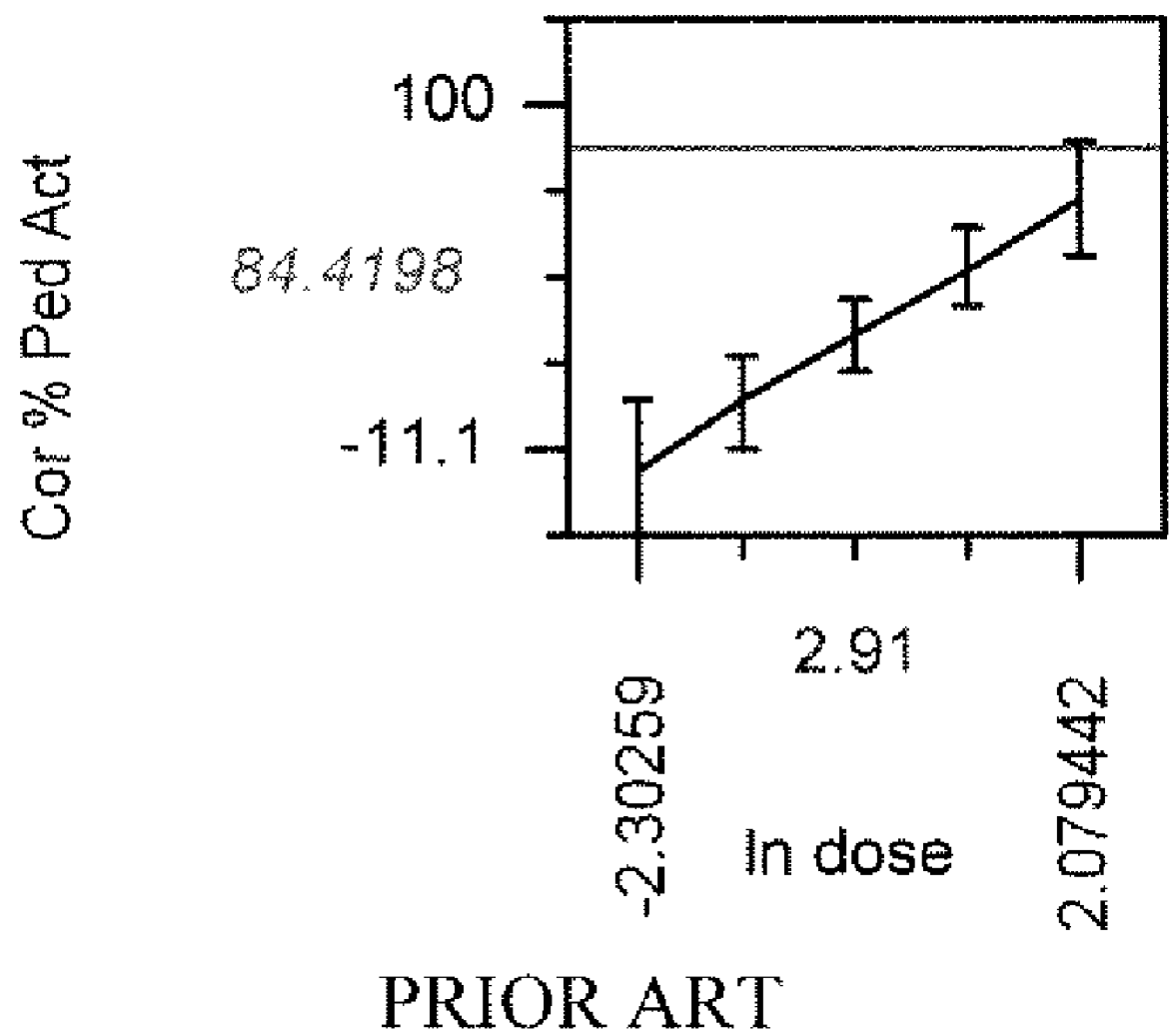
FIG. 6 represents the screening model for 100% pediculicidal activity of the prior art.

For comparison purposes as shown in FIGS. 5-6, the same techniques were applied, retrospectively, to the preferred formulation identified in previous art incorporating a thin addmix system with acetic acid (U.S. Pat. No. 5,902,595) in order to predict the active required for 100% in vitro pediculicidal activity.

Calculations were performed with the resulting data to transform the predicted ln result into citronellyl acetate concentration by fitting the result (x) into the simple following inverse natural log equation:

$e^x = $ % citronellyl acetate

Required citronellyl acetate concentrations were calculated from the predicted values of the prior art and gel formulations. Interestingly for the prior art formulation, no dose could be predicted to yield 100% activity as the response maximum was 85% activity at 18.4% citronellyl acetate.

Surprisingly, however, when the corresponding results for the clear gel formulation of 2.27, 2.19, and 2.74 from the screening model the respective corresponding calculated values were 9.67% citronellyl acetate required for 100% pediculicidal activity, 8.93% for 100% ovicidal activity, and 15.5% required for 100% undeveloped eggs. Interestingly, this specific embodiment of the invention exhibited more lethal qualities with less than half the amount of citronellyl acetate.

Three optimized clear gel formulations were prepared in attempt to identify the most preferred embodiment of the invention. All three formulations incorporated either 10.0% or 12.5% citronellyl acetate and either 15% or 20% IPA. Two formulations used propylene glycol as the base, and both were thickened utilizing Pemulen® and a neutralization step with sodium hydroxide. The third formulation substituted Steol CS-230 (sodium laureth sulfate) for the entire amounts of propylene glycol and glycerin and was thickened through higher levels of Pemulen®. This third formulation also did not incorporate the BHT due to immediate availability issues. Following are the three formulations prepared:

| | Formulation # % (w/w) | | |
|---|---|---|---|
| Ingredient | 1 | 2 | 3 |
| IPA | 15.00 | 15.00 | 20.00 |
| BHT | 0.05 | 0.05 | 0.00 |
| Propylene glycol | 75.06 | 72.56 | 0.00 |
| Steol CS-230 | 0.00 | 0.00 | 65.50 |
| Pemulen ® TR1 | 0.85 | 0.85 | 2.00 |
| Citronellyl acetate | 10.00 | 12.50 | 12.50 |
| Sodium Hydroxide | 0.04 | 0.04 | 0.00 |
| Result Viscosity | 5,750 cps | 4,300 cps | 1,450 cps |

An additional new in vitro pediculicidal activity assessment was implemented in attempt to elucidate preferred embodiments and ultimate confirmation of potential efficacy and assessment of the three formulations. The new method mimicked the ASTM method except that human head lice were collected and used for the evaluation. For the assessment, lice were collected from patients that had recently experienced multiple product failures. This assured a sampling of lice suspected to possess resistance to current treatments. The lice were collected on nylon gauze patches inside of a petri dish. The lice were then used for experimentation within 30 minutes after collection. The lice were separated into groups of 10 and then treated.

The lice were submerged for 1 minute and removed but not rinsed for the remainder of the exposure period (10 minutes for all assessments). The lice were rinsed thoroughly with tap water, blotted dry, and placed on a new, dry piece of nylon gauze. The lice were observed for signs of life under a stereomicroscope at various time intervals up to 3 hours after exposure. Lice were classified as "appeared dead" if no physical movement existed or "alive" if the lice were crawling or otherwise physically moving. Percentages were calculated as shown in FIGS. 7.a.-7.c. for each classification at each time interval.

Surprisingly for formulations #1 and #2, initial observation times indicate a high level of apparent kill, but as time elapsed the lice recovered and lived. Therefore, while these treatments may show efficacy to non-resistant lice, they most likely will not display any efficacy to the resistant ones. However, Formulation #3 (with sodium laureth sulfate, Steol CS-230) apparently overcame the resistance mechanism and resulted in 100% kill. This indicates that the product will most likely be effective against resistant lice in the field. Obviously, the study results identified the surfactant based, clear gel product as the preferred embodiment.

Following is a summary of the preferred gel embodiments, and the most preferred, single embodiment of the invention and the method of producing the product:

| Ingredient | % | Most preferred |
|---|---|---|
| IPA | 5.0-30.0% | 20 |
| BHT | 0.00-0.05 | 0.00 |
| Steol CS-230 | 52.45-88.5% (qs) | 65.5 (qs) |
| Pemulen ® TR1 | 1.5-2.5% | 2.0 |
| Citronellyl acetate | 5.0-15.00 | 12.50 |

| Step | Description |
|---|---|
| 1 | Add alcohol to an adequately sized mixing vessel and begin mixing |
| 2 | While mixing add BHT and mix until completely dissolved |
| 3 | While mixing, add citronellyl acetate and mix for 2 minutes |
| 4 | While mixing, add sodium laureth sulfate (Steol CS-230) and mix for 2 minutes |
| 5 | While mixing, slowly add Pemulen to the vortex and mix until well hydrated and uniformly thickened |

This optimized surfactant based formulation was duplicated and used for comparative pre-clinical toxicology assessments. These assessments were performed and results classified identically to those for prior art (add-mix system, U.S. Pat. No. 5,902,595) for a direct comparison of skin irritation. For the skin irritation testing, an additional exposure time was assessed for the preferred embodiment. Therefore, the study assessed irritation associated with both a 1 and 4-hour exposure to the test product. The Primary Irritation Index (PII) was calculated at 1 and 4-hour exposures. The resulting PIIs were 3.58 for the 1-hour exposure and 4.54 for the 4-hour exposure, both of which classify as a "moderate irritant." Again surprisingly, the preferred embodiment resulted in drastically improved dermal irritation profiles as compared to the prior art that resulted in a PII of 6.75 indicating that the product was "severely irritating".

A variation of the preferred embodiment was prepared with one of the chirally pure terpenes, R- or S-citronellol. The formulations were prepared and tested for in vitro pediculicidal activity using lab lice and the 5 second immersion technique. Interestingly, both formulations resulted in 100% activity. However, a significant difference in the symptoms of exposure and manner of death was observed between the two groups of lice. Immediately after rinsing, there was no difference between the groups. In both cases 3 to 4 lice were beginning to show movement, and some others were inactive but showed gut movement. After 60 minutes, physical signs of exposure began to differentiate. The lice exposed to S-citronellol were basically walking as normal, but 10 lice were showing tonic-clonic spasms similar to that seen for lice exposed to permethrin or other pyrethroids. Only 1 of the lice exposed to R-citronellol appeared alive and normal, 4 others were trying to walk but the rest were completely immobilized. After 180 minutes, 4 four lice exposed to R-citronellol were lying down with "waggling" limbs and the rest remained completely immobilized. For the ones treated with S-citronellol, 2 were lying down with "waggling" limbs, 1 louse walking uncomfortably with stiff limbs, and the remainder were immobile. While both pure enantiomers eventually exhibited 100% pediculicidal activity, the symptoms and physical characteristics after exposure varied drastically.

Scanning electron microscopy was also used to assess possible destruction of the cuticle of lice upon treatment with the preferred embodiment. Lice and eggs were collected before and after exposure to the gel formulation (with racemic citronellyl acetate), analyzed with SEM, and the images were compared to discern cuticle destruction. The imaging clearly revealed cuticle dissolution and surface "erosion." Specifically images showed the most drastic effects around the dorsal column (principal point of thoracic muscular attachment, mainly the muscles that operate the legs) for the treated louse than the untreated. However, images of leg joints show very little or no effects on the tissues of the joints. Comparative images of eggs also revealed evidence of surface destruction. Imaging also revealed a significant difference in opercular pore separation, definition, and height.

The Examples above are intended to be demonstrative, but not exhaustive, of the embodiments contemplated by the present invention. It is intended that other deviations apparent to those skilled in the art from the invention described above are encompassed in the scope and spirit of the invention.

What is claimed is:

1. A pediculicidal and ovicidal composition consisting essentially of citronellyl acetate in a concentration of about 2.5%-15% w/w of the total composition, a viscosity modifier selected from the group consisting of hydroxypropyl cellulose (HPC), hydroxypropyl methylcellulose (HPMC), hydroxyethyl cellulose (HEC), acrylates/C10-30 alkyl acrylate crosspolymers, polyvinylpyrrolidone (PVP), polyvinyl alcohol (PVA), and mixtures thereof, in a concentration of between about 0.1%-10% w/w of the total composition, isopropanol or other short chain organic alcohol in a concentration of between about 10%-30% w/w of the total composition, and a component selected from a group consisting of a non-aqueous co-solvent, a surfactant, and mixtures thereof as the remainder of the composition, wherein said pediculicidal and ovicidal composition is substantially free of acid.

2. The composition of claim 1, wherein the short chain alcohol is isopropanol.

3. The composition of claim 2, wherein the isopropanol is in a concentration of about 20% w/w of the total composition.

4. The composition of claim 1, wherein the isopropanol or other short chain alcohol is in a concentration of between about 15%-25% w/w of the total composition.

5. The composition of claim 1, wherein the citronellyl acetate is in an at least 75% pure form.

6. The composition of claim 1, wherein the citronellyl acetate is in a concentration of between 5%-15% w/w of the total composition.

7. The composition of claim 1, wherein the citronellyl acetate is in a concentration of about 7.5-12.5% w/w of the total composition.

8. The composition of claim 1, wherein the citronellyl acetate is in a concentration of about 10% w/w of the total composition.

9. The composition of claim 1, wherein the viscosity modifier is hydroxypropyl methylcelluose.

10. The composition of claim 1, wherein the viscosity modifier is in a concentration of between about 0.25%-3% w/w of the total composition.

11. The composition of claim 1 wherein the viscosity modifier is used in conjunction with a neutralizing agent.

12. The composition of claim 1, wherein the non-aqueous co-solvent is selected from the group consisting of propylene glycol, butylene glycol, polyethylene glycol, hexylene glycol, methoxypolyethylene glycol, glycerin, and combinations thereof.

13. The composition of claim 1, wherein the surfactant is sodium laureth sulfate, sodium lauryl sulfate, polysorbate or combination thereof.

14. The composition of claim 1, wherein the surfactant is polyoxyethylene sorbitan monolaurate or polysorbate.

15. The composition of claim 1, wherein said pediculicidal and ovicidal composition further includes a component selected from the group consisting of an antioxidant/free radical scavenger, a pH modifier, an antimicrobial agent, a chelating agent, a fragrance, a foaming agent, a conditioning agent, and combinations thereof.

16. The composition of claim 15, wherein said antimicrobial agent is propylparaben.

17. The composition of claim 15, wherein said antimicrobial agent is methylparaben.

18. The composition of claim 15, wherein said fragrance is methyl salicyclate.

* * * * *